United States Patent [19]

Lantzcsh et al.

[11] Patent Number: 5,097,050

[45] Date of Patent: Mar. 17, 1992

[54] ARYL-ALKINYL HALOCYCLOALKYL OXIRANES

[75] Inventors: Reinhard Lantzcsh, Wuppertal; Ernst Kysela, Bergisch-Gladbach; Karl H. Büchel, Burscheid; Stefan Dutzmann, Duesseldorf; Wilheim Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 655,521

[22] Filed: Feb. 14, 1991

Related U.S. Application Data

[62] Division of Ser. No. 376,721, Jul. 7, 1989, Pat. No. 5,025,030.

[30] Foreign Application Priority Data

Jul. 19, 1988 [DE] Fed. Rep. of Germany ....... 3824434

[51] Int. Cl.$^5$ .......................................... C07D 303/08
[52] U.S. Cl. ..................................................... 549/563
[58] Field of Search ......................................... 549/563

[56] References Cited

U.S. PATENT DOCUMENTS

| 4,480,114 | 10/1984 | Regal | 549/563 |
| 4,622,333 | 11/1986 | Lantzsch et al. | 549/563 |
| 4,980,488 | 12/1990 | Stroech et al. | 549/563 |

FOREIGN PATENT DOCUMENTS

| 0108995 | 5/1984 | European Pat. Off. |
| 0298332 | 1/1989 | European Pat. Off. |
| 0351647 | 1/1990 | European Pat. Off. |
| 1183499 | 12/1964 | Fed. Rep. of Germany | 549/563 |

OTHER PUBLICATIONS

Journal of Fluorine Chemistry, Band 41, No. 3, Dec. 1988, pp. 425–427.

*Primary Examiner*—C. Warren Ivy
*Assistant Examiner*—Amelia A. Owens
*Attorney, Agent, or Firm*—Sprung Horn Kramer & Woods

[57] ABSTRACT

An oxirane of the formula

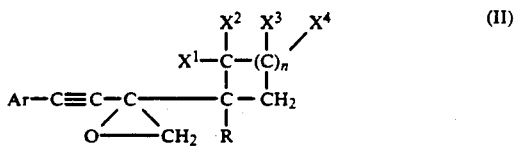

(II)

in which
Ar represents phenyl optionally substituted with from one to three halogen atoms,
R represents alkyl having from 1 to 4 carbon atoms,
$X^1$ represents halogen,
$X^2$ represents hydrogen or halogen,
$X^3$ represents hydrogen or halogen,
$X^4$ represents hydrogen or halogen and
n represents 0 to 1, useful as intermediates for the synthesis of fungicidal hydroxyalkinyl-azoles.

6 Claims, No Drawings

ARYL-ALKINYL HALOCYCLOALKYL OXIRANES

This is a division of application Ser. No. 376,721, filed Jul. 7, 1989, now U.S. Pat. No. 5,025,030.

The present invention relates to novel hydroxyalkinyl-azolyl derivatives, several processes for the preparation thereof, and their use as fungicides.

It has already been disclosed that certain hydroxyalkinyl-azolyl derivatives possess fungicidal properties (cf. EP-OS (European Published Specification) 0,052,424 and EP-OS (European Published Specification) 0,108,995). Thus, for example, 1-(4-chlorophenyl)-3-(1,2,4-triazol-1-yl-methyl)-4,4-dimethyl-pent-1-in-3-ol can be used for combating fungi. The activity of this substance is good, but leaves something to be desired in some cases when low application rates are used.

Novel hydroxy-alkinyl-azolyl derivatives of the formula

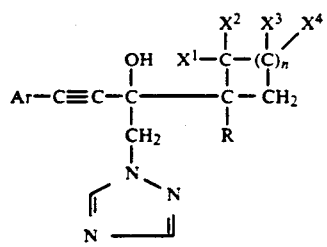

(I)

in which

Ar represents optionally substituted aryl,

R represents alkyl, optionally substituted aryl or optionally substituted aralkyl, $X^1$ represents halogen, $X^2$ represents hydrogen or halogen, $X^3$ represents hydrogen or halogen, $X^4$ represents hydrogen or halogen and n represents 0 or 1, and acid addition salts and metal salt complexes thereof have now been found.

The substances according to the invention contain at least two asymmetrically substituted carbon atoms. They can thus be obtained in optical isomer forms. The invention relates both to the individual isomers and to mixtures thereof.

Furthermore, it has been found that hydroxyalkinyl-azolyl derivatives of the formula (I) and acid addition salts and metal salt complexes thereof are obtained when a) oxiranes of the formula

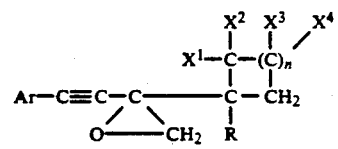

(II)

in which Ar, R, $X^1$, $X^2$, $X^3$, $X^4$ and n have the above-mentioned meaning, are reacted with 1,2,4-triazole of the formula

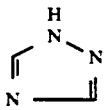

(III)

in the presence of an acid-binding agent and in the presence of a diluent, or b) acetylene derivatives of the formula

Ar—C≡CH (IV)

in which Ar has the abovementioned meaning, are reacted with azolylmethyl ketones of the formula

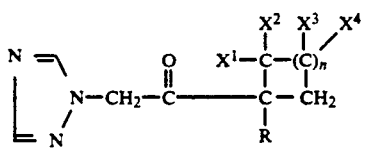

(V)

in which R, $X^1$, $X^2$, $X^3$, $X^4$ and n have the abovementioned meaning, in the presence of a base and in the presence of a diluent and if appropriate in the presence of a phase transfer catalyst, and, if appropriate, an acid or a metal salt are subsequently added onto the resulting compounds of the formula (I).

Finally, it has been found that the novel hydroxyalkinylazolyl derivatives of the formula (I) and the acid addition salts and metal salt complexes thereof possess very good fungicidal properties.

Surprisingly, the substances according to the invention show a better fungicidal activity than 1-(4-chlorophenyl)-3-(1,2,4-triazol-1-yl-methyl)-4,4-dimethyl-pent-1-in-3-ol, which is a previously known active substance having a similar structure and the same direction of action.

Formula (I) provides a general definition of the hydroxy-alkinyl-azolyl derivatives according to the invention. Preferred compounds are those in which Ar represents phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkoximinoalkyl having 1 to 4 carbon atoms in the alkyl moiety and 1 to 4 carbon atoms in the alkoxy moiety, phenoximinoalkyl which has 1 to 4 carbon atoms in the alkyl moiety and which is optionally substituted by alkyl having 1 or 2 carbon atoms and/or halogen, phenyl which is optionally substituted by alkyl having 1 or 2 carbon atoms and/or halogen, or phenoxy which is optionally substituted by alkyl having 1 or 2 carbon atoms and/or halogen, R represents alkyl having 1 to 4 carbon atoms or for phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkoximinoalkyl having 1 to 4 carbon atoms in the alkyl moiety and 1 to 4 carbon atoms in the alkoxy moiety, phenoximinoalkyl which has 1 to 4 carbon atoms in the alkyl moiety and which is optionally substituted by alkyl having 1 or 2 carbon atoms and/or halogen, phenyl which is optionally substituted by alkyl having 1 or 2 carbon atoms and/or halogen, or phenoxy which is optionally substituted by alkyl having 1 or 2 carbon atoms and/or halogen; or R represents benzyl which can be monosubstituted to trisubstituted in the phenyl moiety by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 3 identical or different halogen atoms, halogenoalkylthio having 1 or 2 carbon atoms and 1 to 5 identical or different halogen atoms, alkoximinoalkyl having 1 to 4 carbon atoms in the alkyl moiety and 1 to 4 carbon atoms in the alkoxy moiety, phenoximinoalkyl which has 1 to 4 carbon atoms in the alkyl moiety and which is optionally substituted by alkyl having 1 or 2 carbon atoms and/or halogen, phenyl which is optionally substituted by alkyl having 1 or 2 carbon atoms and/or halogen, or phenoxy which is optionally substituted by alkyl having 1 or 2 carbon atoms and/or halogen;

$X^1$ represents fluorine, chlorine or bromine, $X^2$ represents hydrogen, fluorine, chlorine or bromine, $X^3$ represents hydrogen, fluorine, chlorine or bromine, $X^4$ represents hydrogen, fluorine, chlorine or bromine, and n represents 0 or 1.

Particularly preferred compounds of the formula (I) are those in which

Ar represents phenyl which can be monosubstituted to trisubstituted by identical or different substituents from the series comprising fluorine, chlorine, bromine, methyl, ethyl, isopropyl, tert.-butyl, methoxy, methylthio, trifluoromethyl, trifluoromethoxy, trifluoromethylthio, methoximinomethyl, 1-methoximino-1-ethyl, ethoximinomethyl, phenyl which is optionally substituted by fluorine, chlorine and/or methyl, or phenoxy which is optionally substituted by fluorine, chlorine and/or methyl;

R represents methyl, ethyl, isopropyl, tert.-butyl, or represents phenyl which is optionally monosubstituted to disubstituted by identical or different substituents from the series comprising fluorine, chlorine or methyl, or represents benzyl which can be monosubstituted or disubstituted in the phenyl moiety by identical or different substituents from the series comprising fluorine, chlorine and/or methyl, $X^1$ represents fluorine or chlorine, $X^2$ represents hydrogen, fluorine or chlorine, $X^3$ represents hydrogen, fluorine or chlorine, $X^4$ represents hydrogen, fluorine or chlorine and n represents 0 or 1.

Very particularly preferred compounds of the formula (I) are those in which

Ar represents phenyl which can be monosubstituted to trisubstituted by identical or different substituents from the series comprising fluorine, chlorine, bromine, methyl, ethyl, isopropyl, tert.-butyl, methoxy, methylthio, trifluoromethyl, trifluoromethoxy, trifluoromethylthio, methoximinoethyl, 1-methoximino-1-ethyl, ethoximinomethyl, phenyl which is optionally substituted by fluorine, chlorine and/or methyl, or phenoxy which is optionally substituted by fluorine, chlorine and/or methyl;

R represents methyl, ethyl, phenyl which is optionally monosubstituted or disubstituted by fluorine, chlorine and/or methyl, or for benzyl, $X^1$ represents fluorine or chlorine, $X^2$ represents hydrogen, fluorine or chlorine, $X^3$ represents hydrogen, fluorine or chlorine, $X^4$ represents hydrogen, fluorine or chlorine, and n represents 0 or 1.

Other preferred compounds according to the invention are addition products of acids and those hydroxyalkinyl-azolyl derivatives of the formula (I) in which Ar, R, $X^1$, $X^2$, $X^3$, $X^4$ and n have the meanings which have already been mentioned as being preferred for these radicals or this index.

The acids which can be added on preferably include hydrohalic acids, such as, for example, hydrochloric acid and hydrobromic acid, in particular hydrochloric acid, furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid, 1,5-naphthalenedisulphonic acid or camphorsulphonic acid.

Other preferred compounds according to the invention are addition products of salts of metals of main groups II to IV and of sub-groups I and II and also IV to VIII of the periodic table of the elements and those hydroxyalkinyl-azolyl derivatives of the formula (I) in which Ar, R, $X^1$, $X^2$, $X^3$, $X^4$ and n have the meanings which have already been mentioned as being preferred for these radicals or this index.

Particularly preferred salts in this context are those of copper, zinc, manganese, magnesium, tin, iron and of nickel. Suitable anions of these salts are those which are derived from those acids which lead to physiologically tolerable addition products.

Acids of this type which are particularly preferred in this connection are the hydrohalic acids, such as, for example, hydrochloric acid and hydrobromic acid, furthermore phosphoric acid, nitric acid and sulphuric acid.

Examples of hydroxyalkinyl-azolyl derivatives of the formula (I) which may be mentioned are the substances listed in Table 1 below:

TABLE 1

$$Ar-C\equiv C-\underset{\underset{N\diagdown N}{\overset{CH_2}{|}}}{\overset{\overset{OH}{|}}{C}}-\underset{R}{\overset{X^1}{\underset{|}{C}}}-\underset{CH_2}{\overset{X^2}{\underset{|}{C}}}-\overset{X^3}{\underset{|}{(C)_n}}-X^4 \quad (I)$$

| Ar | X¹ | X² | X³ | X⁴ | n | R |
|---|---|---|---|---|---|---|
| F—⌬— | F | F | — | — | 0 | CH₃ |
| F—⌬— | F | F | — | — | 0 | C₂H₅ |
| F—⌬— | F | F | — | — | 0 | —⌬ |
| F—⌬— | F | F | — | — | 0 | —CH₂⌬ |
| Cl—⌬— | Cl | Cl | — | — | 0 | —⌬ |
| Cl—⌬— | Cl | Cl | — | — | 0 | —CH₂⌬ |
| Cl,Cl—⌬— (2,4-diCl) | Cl | Cl | — | — | 0 | CH₃ |
| Br—⌬— | Cl | Cl | — | — | 0 | CH₃ |
| F—⌬— | Cl | Cl | — | — | 0 | CH₃ |
| (CH₃)₃C—⌬— | Cl | Cl | — | — | 0 | CH₃ |
| CH₃—⌬— | Cl | Cl | — | — | 0 | CH₃ |
| ⌬— | Cl | Cl | — | — | 0 | CH₃ |
| CF₃O—⌬— | Cl | Cl | — | — | 0 | CH₃ |
| o-Cl—⌬— | F | F | — | — | 0 | CH₃ |
| H₃CO—N=CH—⌬— | F | F | — | — | 0 | CH₃ |
| F₃C—⌬— | F | F | — | — | 0 | CH₃ |
| m-Cl—⌬— | F | F | — | — | 0 | CH₃ |
| H₃CO—⌬— | F | F | — | — | 0 | CH₃ |
| H₃CS—⌬— | F | F | — | — | 0 | CH₃ |
| H₃C—⌬— | F | F | — | — | 0 | CH₃ |
| Cl,Cl,Cl—⌬— (3,4,5-triCl) | F | F | — | — | 0 | CH₃ |
| ⌬—⌬— | F | F | — | — | 0 | CH₃ |
| ⌬—O—⌬— | F | F | — | — | 0 | CH₃ |
| 2,4-diCl—⌬— | Cl | F | F | F | 1 | CH₃ |
| (CH₃)₃C—⌬— | Cl | F | F | F | 1 | CH₃ |
| H₃C—⌬— | Cl | F | F | F | 1 | CH₃ |
| F₃CO—⌬— | Cl | F | F | F | 1 | CH₃ |

If 2-[2-(4-chlorophenyl)-ethin-1-yl)]-2-(2,2-difluoro-1-methyl-cycloprop-1-yl)-oxirane and 1,2,4-triazole are used as starting substances, the course of process (a) according to the invention can be illustrated by the following equation:

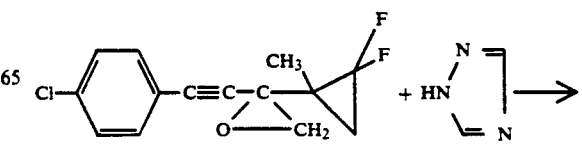

-continued

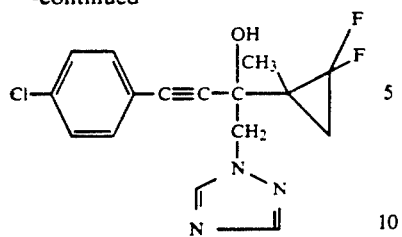

If 2,2-dichloro-1-methyl-cycloprop-1-yl 1,2,4-triazol-1-yl-methyl ketone and 4-chlorophenyl-acetylene are used as starting substances, the course of process (b) according to the invention can be illustrated by the following equation:

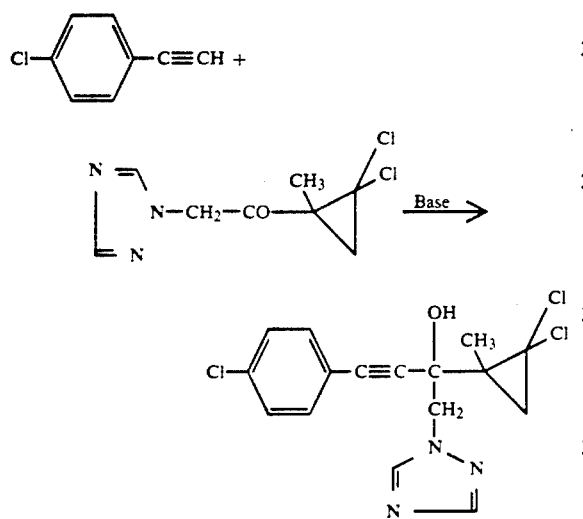

Formula (II) provides a general definition of the oxiranes required as starting substances in process (a) according to the invention. In this formula, Ar, R, $X^1$, $X^3$, $X^4$ and n preferably have those meanings which have already been mentioned in connection with the description of the substances of the formula (I) according to the invention as being preferred for these radicals and this index.

The oxiranes of the formula (II) were hitherto unknown. They can be prepared by a process in which c) cycloalkyl ketones of the formula

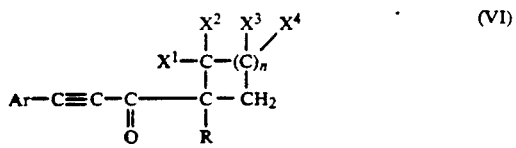

in which Ar, R, $X^1$, $X^2$, $X^3$, $X^4$ and n have the abovementioned meaning are reacted with dimethylsulphonium methylide of the formula $$(CH_3)_2S^{\oplus}CH_2^{\ominus} \qquad (VII)$$

in the presence of a diluent.

The cycloalkyl ketones of the formula (VI) required as starting substances for carrying out process (c) were hitherto unknown. They can be prepared by a process in which d) acetylene derivatives of the formula $$Ar-C\equiv CH \qquad (IV)$$

in which Ar has the abovementioned meaning are reacted with cycloalkyl-carbonyl halides of the formula

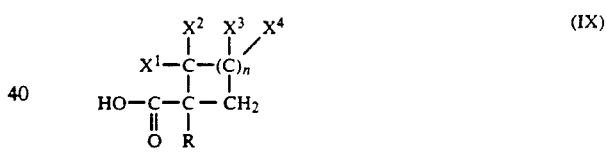

in which R, $X^1$, $X^2$, $X^3$, $X^4$ and n have the abovementioned meaning and Hal represents chlorine or bromine in the presence of a catalyst and in the presence of an acid-binding agent and also in the presence of a diluent.

Formula (IV) provides a general definition of the acetylene derivatives required as starting substances in process (d) and also in process (b) according to the invention. In this formula, Ar preferably has those meanings which have already been mentioned in connection with the description of the substances of the formula (I) according to the invention as being preferred for this radical.

The acetylene derivatives of the formula (IV) are known or can be prepared by processes which are known in principle.

Some of the cycloalkylcarbonyl halides of the formula (VIII) required as reactants in process (d) are known. They can be prepared by a process in which cycloalkylcarboxylic acids of the formula

in which
R, $X^1$, $X^2$, $X^3$, $X^4$ and n have the abovementioned meaning are reacted with chlorinating or brominating agents, such as thionyl chloride, sulphuryl chloride, phosphorus trichloride, thionyl bromide or phosphorus tribromide, if appropriate in the presence of a diluent, such as chloroform or carbon tetrachloride, and if appropriate in the presence of a reaction accelerator such as, for example, dimethylformamide, at temperatures between 0° C. and 60° C.

Some of the cycloalkanecarboxylic acids of the formula (IX) are known (cf. J. Amer. Chem. Soc. 71, 493 (1949), J. Org. Chem. 32, 1290 (1967), J. Org. Chem. 51, 1926 (1986), J. Chem. Res. Synop. 1986, 3, 114 and EP-OS (European Published Specification) 0,043,950).

The cycloalkanecarboxylic acids of the formula (IX) in which n represents 1 can be prepared by a process in which acrylic ester derivatives of the formula $$CH_2=C-COOR^1 \qquad (X)$$
$$\phantom{CH_2=}R$$

in which

R has the abovementioned meaning and
R¹ represents alkyl having 1 to 4 carbon atoms are reacted with ethylene derivatives of the formula

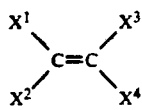
(XI)

in which X¹, X², X³ and X⁴ have the abovementioned meaning, if appropriate in the presence of a diluent, and if appropriate in the presence of hydroquinone, at temperatures between −70° C. and 150° C. and under a protective gas atmosphere under a pressure of between 1 and 100 bar, and the resulting esters of the formula

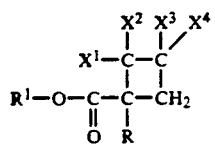
(XII)

in which R, R¹, X¹, X², X³ and X⁴ have the abovementioned meaning are reacted with bases, such as, for example, potassium hydroxide or sodium hydroxide, in the presence of a diluent, such as, for example, methanol or ethanol, at temperatures between 0° C. and 80° C., and the mixture is acidified.

The cycloalkanecarboxylic acids of the formula (IX) in which n represents 0 can be prepared by a process in which vinylcyclopropane derivatives of the formula

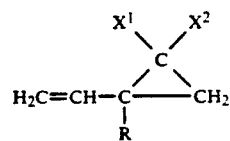
(XIII)

in which
R, X¹ and X² have the abovementioned meaning are reacted with oxidants, such as, for example, potassium permanganate, in the presence of a diluent, such as, for example, water, at temperatures between 0° C. and 50° C.

The compounds of the formula (X), (XI) and (XIII) are known or can be prepared by processes known in principle.

Suitable catalysts for carrying out process (d) are all reaction accelerators customary for reactions of this type. Copper salts, such as, for example, copper(I) bromide, can preferably be used.

Possible acid-binding agents for carrying out process (d) are all bases customary for reactions of this type. Alkali metal hydroxides, such as sodium hydroxide and potassium hydroxide, furthermore tertiary amines, such as triethylamine, can preferably be used.

Diluents which can be used for carrying out process (d) are all customary inert organic solvents. Aliphatic or aromatic hydrocarbons, such as pentane, hexane, benzene, toluene and xylene, can preferably be used.

When carrying out process (d), the reaction temperatures can be varied within a relatively wide range. In general, the process is carried out at temperatures between 0° C. and 150° C., preferably between 20° C. and 120° C.

Like the other processes according to the invention, process (d) is generally carried out under atmospheric pressure. However, it is also possible in each case to carry out the reaction under increased or reduced pressure.

For carrying out process (d), a procedure is generally followed in which 1 mole of cycloalkyl-carbonyl halide of the formula (VIII) and a catalytic amount of reaction accelerator are employed per mole of acetylene derivative of the formula (IV). However, it is also possible to use one or the other component in excess. Moreover, it is expedient to carry out the procedure under a protective gas atmosphere.

Dimethylsulphonium methylide, which has the formula (VII) and is suitable as reactant for process (c), is known (cf. Heterocycles 8, 397 (1977)). In the above reaction, it is employed in the freshly prepared state by preparing it in situ, for example from trimethyl sulphonium halide or trimethylsulphonium methyl sulphate, in the presence of a strong base, such as, for example, sodium hydride, sodium amide, sodium methoxide, potassium tert.-butoxide or potassium hydroxide, in the presence of a diluent, such as tert.-butanol or dimethyl sulphoxide.

Possible diluents for carrying out process (c) are inert organic solvents. Alcohols, such as tert.-butanol, ethers, such as tetrahydrofuran or dioxane, furthermore aliphatic and aromatic hydrocarbons, such as benzene, toluene or xylene, and also strongly polar solvents, such as dimethyl sulphoxide, can preferably be used.

When carrying out process (c), the reaction temperatures can be varied within a relatively wide range. In general, the process is carried out between 0° C. and 100° C., preferably between 10° C. and 60° C.

When carrying out process (c), 1 to 3 moles of dimethylsulphonium methylide of the formula (VII) are generally employed per mole of cycloalkyl ketone of the formula (VI). The oxiranes of the formula (II) are isolated by customary methods.

1,2,4-Triazole, which has the formula (III) and is required as reactant for carrying out process (a) according to the invention, is a generally known compound of organic chemistry.

Possible acid-binding agents for carrying out process (a) according to the invention are all customary acid acceptors. Alkali metal carbonates and hydrogen carbonates, such as sodium carbonate, potassium carbonate or sodium hydrogen carbonate, furthermore alkali metal hydroxides and alkali metal alkoxides, such as sodium hydroxide, potassium hydroxide, sodium methoxide or potassium tert.-butoxide, furthermore tertiary aliphatic or aromatic amines, such as triethylamine, N,N-dimethyl-cyclohexylamine, N,N-dimethyl-benzylamine and pyridine, and furthermore cyclic amines, such as 1,5-diaza-bicyclo[4.3.0]-non-5-ene (DBN), 1,8-diaza-bicyclo[5.4.0]undec-7-ene (DBU) and 1,4-diazabicyclo[2.2.2]octane (DABCO) can preferably be used.

Suitable diluents for carrying out process (a) according to the invention are all inert organic solvents. Nitriles, such as, in particular, acetonitrile; aromatic hydrocarbons, such as benzene, toluene and dichlorobenzene; formamides, such as, in particular, dimethylformamide, and also hexamethylphosphoric triamide, can preferably be used.

When carrying out process (a) according to the invention, the reaction temperatures can be varied within a relatively wide range. In general, the process is carried out at temperatures of between 0° C. and 200° C., preferably between 50° and 150° C.

When carrying out process (a) according to the invention, 1 to 4 moles of 1,2,4-triazole of the formula (III) and 1 to 2 moles of acid-binding agent are generally employed per mole of oxirane of the formula (II). The end products are isolated by customary methods.

Formula (V) provides a general definition of the azolylmethyl ketones required as reactants for carrying out process (b) according to the invention. In this formula, R, $X^1$, $X^2$, $X^3$, $X^4$ and n preferably have those meanings which have already been mentioned in connection with the description of the compounds of the formula (I) according to the invention as being preferred for these radicals and the index n.

The azolylmethyl ketones of the formula (V) were hitherto unknown. They can be prepared by a process in which e) halogenoketones of the formula

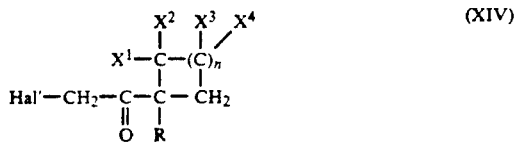

in which R, $X^1$, $X^2$, $X^3$, $X^4$ and n have the abovementioned meaning and Hal' represents chlorine or bromine are reacted with 1,2,4-triazole of the formula

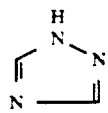

(III)

in the presence of an acid-binding agent and in the presence of a diluent.

The halogenoketones of the formula (XIV) which are required as starting substances in process (e) can be prepared by a process in which f) methyl cycloalkyl ketones of the formula

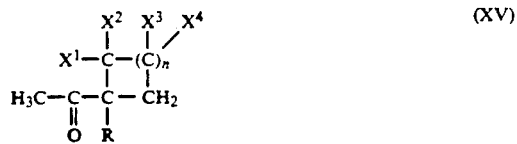

in which R, $X^1$, $X^2$, $X^3$, $X^4$ and n have the abovementioned meaning are reacted with chlorinating agents or brominating agents in the presence of a diluent.

The methyl cycloalkyl ketones of the formula (XV) which are required as starting substances in process (f) can be prepared by a process in which cycloalkylcarboxylic acids of the formula

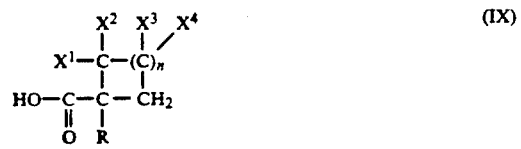

in which R, $X^1$, $X^2$, $X^3$, $X^4$ and n have the abovementioned meaning are reacted with methyl-lithium in the presence of a diluent, such as, for example, diethyl ether, at temperatures between −80° C. and +20° C.

Suitable chlorinating agents and brominating agents for process (f) are all chlorinating and brominating reagents which are customary for reactions of this type. Sulphuryl chloride, sulphuryl bromide and bromine can preferably be used.

Possible diluents for process (f) are all inert organic solvents which are customary for reactions of this type. Halogenated aliphatic hydrocarbons, such as methylene chloride, chloroform and carbon tetrachloride, are preferably suitable.

In process (f), the reaction temperatures can be varied within a certain range. In general, the process is carried out at temperatures between −10° C. and +60° C., preferably between 0° C. and +40° C.

When carrying out process (f), a stoichiometric amount or even a small excess of chlorinating or brominating agent is generally employed per mole of methyl cycloalkyl ketone of the formula (XV). Working up is carried out by customary methods. In general, a procedure is followed in which the reaction mixture is washed in succession with dilute aqueous sodium hydrogen carbonate solution and water, then dried and concentrated.

Suitable acid-binding agents and diluents for carrying out process (e) are all those substances which have already been mentioned in connection with carrying out process (a) according to the invention as being preferred.

When carrying out process (e), the reaction temperatures can be varied within a relatively wide range. In general, the process is carried out at temperatures between 0° C. and 150° C., preferably between 20° C. and 120° C.

When carrying out process (e), 1 to 3 moles of 1,2,4-triazole of the formula (III) and 1 to 2 moles of acid-binding agent are generally employed per mole of halogenoketone of the formula (XIV). Working up is carried out by customary methods. In general, a procedure is followed in which the reaction mixture is concentrated—if appropriate after previously filtering off any salts which have been separated out—the residue is then taken up in a slightly water-miscible organic solvent, and the resulting solution is washed, dried and then concentrated.

Possible diluents for carrying out process (b) according to the invention are inert organic solvents. Ethers, such as tetrahydrofuran, dioxane, ethylene glycol diethyl ether, diethylene glycol dimethyl ether and diethyl ether, furthermore aromatic hydrocarbons, such as benzene, chlorobenzene, o-dichlorobenzene and toluene, moreover aliphatic hydrocarbons, such as hexane, cyclohexane and methylene chloride, additionally acid amides, such as dimethylformamide and hexamethylphosphoric triamide, furthermore sulphoxides, such as dimethyl sulphoxide, and also nitriles, such as acetonitrile, and even acetals, such as butyraldehyde dibutyl acetal, acetaldehyde dibuty acetal and methylethyldioxolane.

Suitable bases for carrying out process (b) according to the invention are strong bases. Alkali metal amides, alkali metal hydrides and alkali metal hydroxides, such as, for example, sodium amide, sodium hydroxide or sodium hydride, and potassium amide, potassium hydroxide or potassium hydride, furthermore alkali metal alkoxides, such as potassium tert.-butoxide, moreover Grignard compounds, such as ethylmagnesium bromide, or other organometal compounds, such as n-butyllithium, can preferably be used.

Suitable phase transfer catalysts for carrying out process (b) according to the invention are preferably ammonium or phosphonium compounds, such as, for example, tetrabutylammonium bromide or tetrabutylammonium chloride and triethyl-benzyl-ammonium chloride.

When carrying out process (b) according to the invention, the reaction temperatures can be varied within a relatively wide range. In general, the process is carried out at temperatures between −80° C. and +80° C., preferably between −10° C. and +40° C. When the phase transfer catalyst is used, the process is generally carried out at between 40° C. and 150° C., preferably between 70° C. and 120° C.

When carrying out process (b) according to the invention, the reactants are preferably employed in equimolar amounts. The end products are worked up and isolated by customary methods.

The substances of the formula (I) which can be obtained by processes (a) and (b) according to the invention can be converted to acid addition salts or metal salt complexes.

Possible acids for the preparation of acid addition salts of the compounds of the formula (I) are preferably those which have already been mentioned in connection with the description of the acid addition salts according to the invention as being preferred acids:

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtering off and, if appropriate, purified by washing with an inert organic solvent.

Possible salts of metals for the preparation of metal salt complexes of the compounds of the formula (I) are preferably those which have already been mentioned in connection with the description of the metal salt complexes according to the invention as being preferred metal salts.

The metal salt complexes of the compounds of the formula (I) can be obtained in a simple manner by customary processes, thus, for example, by dissolving the metal salt in alcohol, for example ethanol, and adding the solution to compounds of the formula (I). Metal salt complexes can be isolated in a known manner, for example by filtering off, and, if appropriate, they can be purified by recrystallization.

The active substances according to the invention exhibit a powerful microbicidal action and can be employed as fungicides.

Fungicidal agents in plant protection are employed for combating plasmodiophoromycetes, Oomycetes, Chytridiomycetes, Zygomycetes, Ascomycetes, Basidiomycetes and Deuteromycetes.

Some causative organism of fungal and bacterial diseases which come under the generic names listed above may be mentioned as examples, but not by way of limitation:

Xanthomonas species, such as, for example, *Xanthomonas oryzae*; Pseudomonas species, such as, for example, *Pseudomonas lachrymans*; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubense*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, *Venturia inaequalis*; Pyrenophora species, such as *Pyrenophora teres* or *P. graminea*; (conidia form: Drechslera, syn: Helminthosporium); Cochliobolus species, such as, for example, *Cochliobolus sativus*; (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as *Ustilago nuda* or *Ustilago avenae*; Pellicularia species, such as *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal diseases, such as *Erysiphe graminis*, furthermore rice diseases, such as *Pyricularia oryzae*, and rust diseases, such as *Uromyces appendiculatus*.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02% by weight, are required at the place of action.

The preparation and use of the active compounds according to the invention are evident from the examples which follow.

PREPARATION EXAMPLES

EXAMPLE 1

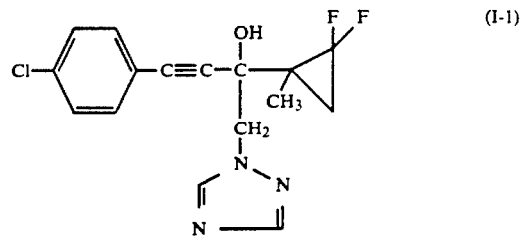

3.5 g of 2-[2-(4-chlorophenyl)-ethin-1-yl)]-2-(2,2-difluoro-1-methyl-cycloprop-1-yl)-oxirane are added at room temperature to a stirred mixture of 0.9 g (0.013 mol) of 1,2,4-triazole, 1.8 g (0.013 mol) of ground potassium carbonate and 30 ml of acetonitrile. The mixture is refluxed for 8 hours, then cooled, diluted with water and extracted three times using methylene chloride. The combined organic phases are washed with water, then dried and concentrated under reduced pressure. In this manner, 3.8 g of a dark oil are obtained which is purified by column chromatography (petroleum ether-/ethyl acetate=2:1) on silica gel. 2.1 g (48% of theory) of 1-(4-chlorophenyl)-3-(2,2-difluoro-1-methyl-cycloprop-1-yl)-4-(1,2,4-triazol-1-yl)-but-1-in-3-ol remain in form of a solid substance of melting point 113°–115° C.

Preparation of Starting Substances

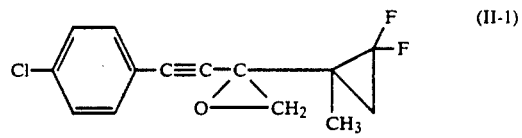

A mixture of 13 g of dimethyl sulphide and 4.8 g of dimethyl sulphate is initially stirred for 2 hours at room temperature, and 18 ml of tert.-butanol and 8.9 g of 2-(4-chlorophenyl)-ethin-1-yl 2,2-difluoro-1-methyl-cycloprop-1-yl ketone are then added. The mixture is stirred for 30 minutes at room temperature and cooled to 10° C., and a solution of 4.5 g of potassium tert.-butoxide in 32 ml of tert.-butanol is added dropwise to the stirred mixture in the course of one hour. Stirring of the reaction mixture is continued for 3 hours at 10° C., and the mixture is then concentrated by stripping off the solvent under reduced pressure. The residue is taken up in methylene chloride, and the mixture is washed three times with water, dried and reconcentrated under reduced pressure. 6.4 g (68% of theory) of 2-[2-(4-chlorophenyl)-ethin-1-yl]-2-(2,2-difluoro-1-methyl-cycloprop-1-yl)-oxirane remain in the form of an oil which is reacted further without additional purification.

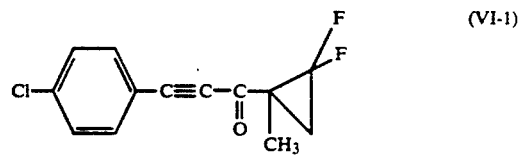

13.7 g (0.1 mol) of p-chlorophenyl-acetylene are added to a mixture of 10.1 g (0.1 mol) of triethylamine, 1.4 g (0.01 mol) of copper(I) bromide and 55 ml of toluene, and the mixture is stirred for 30 minutes at room temperature under argon. After the reaction mixture has been heated to 55° C., 15.5 g (0.1 mol) of 1-methyl-2,2-difluorocyclopropanecarbonyl chloride are added dropwise. After this, the mixture is stirred for 8 hours at 90° C., and then cooled and filtered. The filtrate is washed with dilute aqueous hydrochloric acid and water in succession and concentrated under reduced pressure. 19.2 g of a dark oil remain which is distilled using a bulb tube. A yellow oil, which solidifies on standing, distils over at 0.1 mbar and a jacket temperature of 120° C. 8.4 g (33% of theory) of 2-(4-chlorophenyl)-ethin-1-yl 2,2-difluoro-1-methyl-cycloprop-1-yl ketone of melting point 67°–68° C. are obtained.

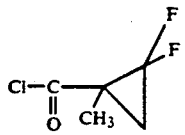
(VIII-1)

A mixture of 250 g (1.8 mol) of 2,2-difluoro-1-methyl-cyclopropanecarboxylic acid and 700 ml of thionyl chloride is slowly heated in a distillation apparatus, during which process excess thionyl chloride distils over first and the desired product later. In this manner, 215 g (77% of theory) of 2,2-difluoro-1-methylcyclopropanecarbonyl chloride are obtained in form of a liquid of boiling point 121°–122° C.

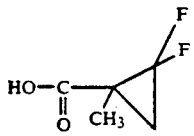
(IX-1)

2.3 kg (14.47 mol) of potassium permanganate are added in portions to 840 g (7.12 mol) of 2,2-difluoro-1-methyl-1-vinyl-cyclopropane in 10 l of water. The mixture is stirred for 36 hours, and the manganese dioxide is filtered off and washed thoroughly with water. The filtrate is acidified using concentrated hydrochloric acid and extracted using dichloromethane. The organic phase is dried, the solvent is then removed in vacuo and the residue is distilled.

In this way, 750 g (77% of theory) of 2,2-difluoro-1-methylcyclopropanecarboxylic acid melting point 59°–61° C. are obtained.

EXAMPLE 2

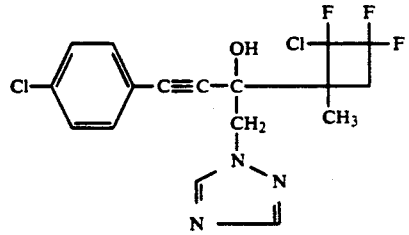
(I-2)

31.8 g of 2-[2-(4-chlorophenyl)-ethin-1-yl]-2-(2,3,3-trifluoro-2-chloro-1-methylcyclobut-1-yl)-oxirane are added at room temperature to a stirred mixture of 6.4 g of 1,2,4-triazole, 12.6 g of ground potassium carbonate and 300 ml of acetonitrile. The reaction mixture is refluxed for 12 hours, and then cooled and filtered. The filtrate is concentrated under reduced pressure, and the remaining residue is purified by column chromatography (ethyl acetate) on silica gel. 29 g (75.5% of theory) of 1-(4-chlorophenyl)-3-(2,3,3-trifluoro-2-chloro-1-methyl-cyclobut-1-yl)-4-(1,2,4-triazol-1-yl)-but-1-in-3-ol are obtained in form of a viscous oil.

Preparation of the Starting Substances

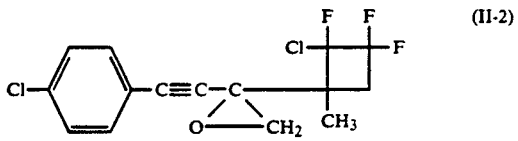
(II-2)

A mixture of 37.2 g of dimethyl sulphide and 13.2 g of dimethyl sulphate is stirred for 2 hours at room temperature, and 25 ml of tert.-butanol and 16.05 g of 2-(4-chlorophenyl)-ethin-1-yl 2,3,3-trifluoro-2-chloro-1-methylcyclobut-1-yl ketone are then added. The mixture is stirred for 30 minutes at room temperature and cooled to 10° C., and a solution of 6.4 g of potassium tert.-butoxide in 45 ml of tert.-butanol is added dropwise to the stirred mixture in the course of 1.25 hours. Stirring of the reaction mixture is continued for 3 hours at 10° C., and the mixture is then concentrated by stripping off the diluent under reduced pressure. The residue is taken up in methylene chloride, and the mixture is washed three times with water, dried and reconcentrated under reduced pressure. 31.8 g (95% of theory) of 2-[2-(4-chlorophenyl)ethin-1-yl]-2-(2,3,3-trifluoro-2-chloro-1-methyl-cyclobut-1-yl)-oxirane remain in form of an oil which is reacted further without additional purification.

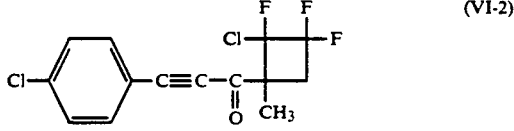
(VI-2)

41 g of p-chlorophenyl-acetylene are added to a mixture of 30.3 g (0.3 mol) of triethylamine, 4.5 g of copper(I) bromide and 250 ml of toluene, and the mixture is stirred for 30 minutes at room temperature and under argon. After the reaction mixture has been heated to 50° C., 66.3 g of 1-methyl-2-chloro-2,3,3-trifluoro-cyclobutane-1-carbonyl chloride are added dropwise. The stirred mixture is then heated for 12 hours at 85° C. and then cooled and filtered. The filtrate is washed in succession with dilute aqueous hydrochloric acid and water, and then dried and concentrated under reduced pressure. The residue remaining is washed with hexane. 65 g (67.5% of theory) of 2-[2-(4-chlorophenyl)-ethin-1-yl] 2-(2,3,3-trifluoro-1-chloro-1-methyl-cyclobut-1-yl) ketone are obtained in form of a solid substance of melting point 69° C.

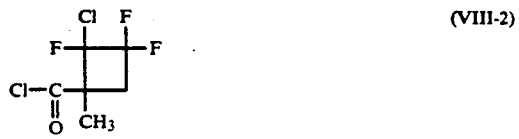
(VIII-2)

One drop of dimethylformamide is added to a mixture of 91.2 g (0.45 mol) of 1-methyl-2,3,3-trifluoro-2-chlorocyclobutane-1-carboxylic acid and 450 ml of chloroform. After this, 80.3 g (0.675 mol) of thionyl chloride are added dropwise at 25°-30° C. with stirring, and the stirred mixture is heated to the boil. After 6 hours the mixture is cooled, the solvent is stripped off, and the residue is subjected to fractional distillation under reduced pressure. 75 g (75% of theory) of 1-methyl-2-chloro-2,3,3-trifluoro-cyclobutane-1-carbonyl chloride are obtained in form of a liquid of boiling point 65°-70° C. at 20 mbar.

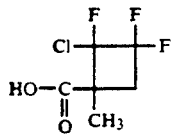
(IX-2)

108.3 g (0.5 mol) of methyl 1-methyl-2-chloro-2,3,3-trifluoro-cyclobutane-1-carboxylate are added dropwise at 20°-25° C. in the course of 15 minutes to a stirred solution of 127.3 g of potassium hydroxide in 540 ml of methanol. Stirring is continued for 12 hours at 20°-25° C., and part of the methanol is then stripped off under reduced pressure. The residue is diluted with water, and the mixture is extracted using methylene chloride. The aqueous phase is acidified using dilute hydrochloric acid and extracted using methylene chloride. The combined organic phases are dried and concentrated under reduced pressure. 93.3 g of an oil are obtained which consists of 99% 1-methyl-2-chloro-2,3,3-trifluoro-cyclobutane-1-carboxylic acid. The yield is thus calculated at 90% of theory.

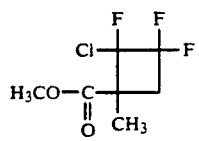
(XII-1)

174 g (1.74 mol) of methyl methacrylate and 1.5 g of hydroquinone are initially introduced into an autoclave, and 200 g (1.74 mol) of trifluorochloroethylene are added at −70° C. 7 bar of nitrogen are injected, and the mixture is then heated to 140° C. The pressure which is established at this temperature is increased to 28 bar by injecting more nitrogen. The mixture is maintained at 140° C. for 17 hours and then allowed to cool, the pressure is released, and the mixture is distilled. In this process, 203 g (54% of theory) of methyl 1-methyl-2-chloro-2,3,3-trifluoro-cyclobutane-1-carboxylate are obtained in form of a liquid of boiling point 57° C. at 17 mbar.

The compounds of the formula (I) listed in Table 2 below are also prepared following the methods indicated in Examples 1 and 2.

TABLE 2

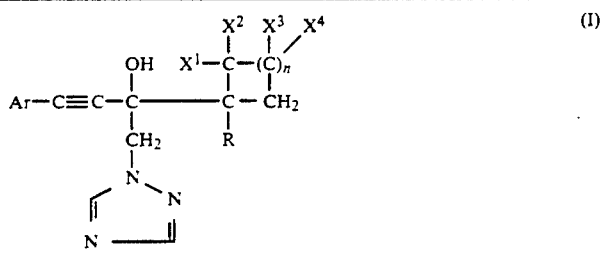
(I)

| Example No. | Compound No. | Ar | $X^1$ | $X^2$ | $X^3$ | $X^4$ | n | R | Physical constant |
|---|---|---|---|---|---|---|---|---|---|
| 3 | I-3 | Cl—⌬— | Cl | Cl | — | — | 0 | $CH_3$ | resin*) |
| 4 | I-4 | ⌬— | Cl | F | F | F | 1 | $CH_3$ | resin**) |
| 5 | I-5 | F—⌬— | Cl | F | F | F | 1 | $CH_3$ | resin |
| 6 | I-6 | Cl—⌬— | Cl | F | — | — | 0 | $CH_3$ | resin |
| 7 | I-7 | Cl—⌬— | F | H | — | — | 0 | $CH_3$ | resin |

TABLE 2-continued

| 8 | I-8 | Br—⟨C6H4⟩— | Cl | F | F | F | 1 | CH₃ | m.p. 78° C. |
|---|-----|-----|----|---|---|---|---|-----|-------------|

*)The compound (I-3) is characterized by its ¹H-NMR spectrum (CDCl₃) as a mixture of 2 diastereomer pairs 1.25 and 1.9 ppm ⎫
1.5 and 2.4 ppm ⎭ cyclopropane-CH₂

1.7 ppm (d) CH₃
4.0 ppm OH
4.7 amd 5.3 ppm (m) CH₂
7.3 ppm aromatic
7.9–8.3 ppm (dd) triazole-H

**)Compound (I-4) contains 3 asymmetric carbon atoms: thus, an isomer mixture is obtained which was characterized by the ¹H-NMR spectrum (CDCl₃):

| 1.65 ppm | CH₃ group |
| 2.3–3.6 ppm | cyclobutane-CH₂ |
| 4.5 ppm | —CH₂-(triazole) |
| 7.2–7.4 ppm | 5H(aromatic) |
| 7.95 and 8.3 ppm | 2H(triazole) |

The compounds of the formula (VI) which are listed in Table 3 below are also prepared following the methods indicated in Examples 1 and 2.

EXAMPLE A

Erysiphe test (barley)/protective

TABLE 3

$$Ar-C\equiv C-\underset{\underset{R}{|}}{\overset{O}{\overset{\|}{C}}}-\underset{|}{\overset{X^2}{\underset{|}{C}}}-\overset{X^3}{\underset{|}{(C)_n}}\overset{X^4}{\diagup}-CH_2 \qquad (VI)$$

with X¹—C— attached to the central carbon

| Example No. | Compound No. | Ar | X¹ | X² | X³ | X⁴ | n | R | Physical constant |
|---|---|---|---|---|---|---|---|---|---|
| 6 | VI-3 | C₆H₅— | Cl | F | F | F | 1 | CH₃ | $n_D^{20}$ = 1,5191 |
| 7 | VI-4 | F—C₆H₄— | Cl | F | F | F | 1 | CH₃ | G.p. = 160° C./2,5 mbar |
| 8 | VI-5 | Cl—C₆H₄— | Cl | Cl | — | — | 0 | CH₃ | m.p. = 87° C. |
| 9 | VI-6 | Cl—C₆H₄— | Cl | F | — | — | 0 | CH₃ | m.p. = 65° C. |

In the following Use Examples, the compound listed below was employed as comparison substance:

Cl—⟨C₆H₄⟩—C≡C—C(OH)(CH₂-triazole)—C(CH₃)₂—CH₃ = (A)

(disclosed in EP-OS (European Published Specification) 0,052,424).

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f. sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, compound (I-1) according to the invention shows a considerably better action than comparison substance (A).

EXAMPLE B

Uromyces test (dwarf bean)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous uredospore suspension of the bean rust causative organism (*Uromyces appendiculatus*) and remain in a dark humidity chamber at 20° to 22° C. and 100% relative atmospheric humidity for 1 day.

The plants are then placed in a greenhouse under intensive illumination at 20° to 22° C. and a relative atmospheric humidity of 70 to 80% for 9 days.

Evaluation is carried out 10 days after the inoculation.

In this test, compound (I-1) according to the invention shows a better activity than comparison substance (A).

EXAMPLE C

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, compounds (I-1) and (I-2) according to the invention show a considerably better activity than comparison substance (A).

It is understood that the specification and examples are illustrative but not limitative of the present invention and that other embodiments within the spirit and scope of the invention will suggest themselves to those skilled in the art.

What is claimed is:

1. An oxirane of the formula

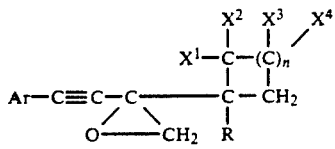

in which
Ar represents phenyl optionally substituted by 1 to 3 halogen atoms,
R represents alkyl having from 1 to 4 carbon atoms,
$X^1$ represents halogen,
$X^2$ represents hydrogen or halogen,
$X^3$ represents hydrogen or halogen,
$X^4$ represents hydrogen or halogen and
n represents 0 or 1.

2. A compound according to claim 1, in which
Ar represents phenyl which can be monosubstituted to trisubstituted by identical or different substituents from the series comprising fluorine, chlorine and bromine,
R represents methyl, ethyl, isopropyl or tert.-butyl,
$X^1$ represents fluorine or chlorine,
$X^2$ represents hydrogen, fluorine or chlorine,
$X^3$ represents hydrogen, fluorine or chlorine,
$X^4$ represents hydrogen, fluorine or chlorine and
n represents 0 or 1.

3. A compound according to claim 1, in which
Ar represents phenyl which can be monosubstituted to trisubstituted by identical or different substituents from the series comprising fluorine, chlorine and bromine,
R represents methyl or ethyl,
$X^1$ represents fluorine or chlorine,
$X^2$ represents hydrogen, fluorine or chlorine,
$X^3$ represents hydrogen, fluorine or chlorine,
$X^4$ represents hydrogen, fluorine or chlorine, and
n represents 0 or 1.

4. A compound according to claim 1, wherein such compound is represented by the formula

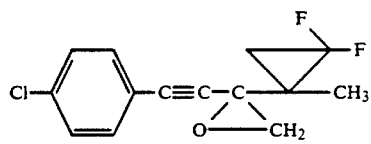

5. A compound according to claim 1, wherein such compound is represented by the formula

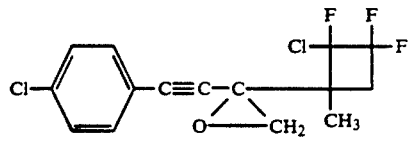

6. A compound according to claim 1, wherein such compound is represented by the formula

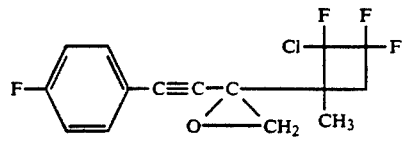

* * * * *